(12) United States Patent
Corbin

(10) Patent No.: US 10,051,863 B2
(45) Date of Patent: *Aug. 21, 2018

(54) METHODS FOR APPLE SCAB CONTROL

(71) Applicant: Valent U.S.A., Corporation, Walnut Creek, CA (US)

(72) Inventor: Billy R. Corbin, Greenville, MS (US)

(73) Assignee: VALENT U.S.A., CORPORATION, Walnut Creek, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/841,899

(22) Filed: Dec. 14, 2017

(65) Prior Publication Data

US 2018/0103639 A1    Apr. 19, 2018

Related U.S. Application Data

(63) Continuation of application No. 15/198,542, filed on Jun. 30, 2016, now Pat. No. 9,844,221.

(60) Provisional application No. 62/188,266, filed on Jul. 2, 2015.

(51) Int. Cl.
*A01N 43/56* (2006.01)
*A01N 43/653* (2006.01)

(52) U.S. Cl.
CPC ........... *A01N 43/56* (2013.01); *A01N 43/653* (2013.01)

(58) Field of Classification Search
CPC ....... A01N 43/56; A01N 25/30; A01N 43/653
See application file for complete search history.

(56) References Cited

U.S. PATENT DOCUMENTS

| 3,931,413 | A | 1/1976 | Frick |
| 4,134,987 | A | 1/1979 | Huppatz |
| 5,093,347 | A | 3/1992 | Graneto et al. |
| 8,580,836 | B2 | 11/2013 | Matsuzaki et al. |
| 8,765,636 | B2 | 7/2014 | Dahmen et al. |
| 9,844,221 | B2 * | 12/2017 | Corbin, Jr. ............. A01N 43/56 |
| 2011/0110906 | A1 | 5/2011 | Andersch et al. |
| 2012/0004100 | A1 | 1/2012 | Hungenberg et al. |
| 2014/0038823 | A1 | 2/2014 | Dahmen et al. |

OTHER PUBLICATIONS

Watson, "The Science of Systematic Bark Sprays", issued May/Jun. AA 2013, posted on May 31, 2013, pp. 1-3.
Rosenberger, "Results of 2008 Fruit Fungicide Trials in the Hudson Valley" Final Report on Field Trials Dec. 10, 2008, pp. 1-48.

* cited by examiner

*Primary Examiner* — Sudhakar Katakam
(74) *Attorney, Agent, or Firm* — Wood, Phillips, Katz, Clark & Mortimer

(57) ABSTRACT

The present invention relates to methods for controlling apple scab caused by *Venturia inaequalis* comprising spraying the bark of an apple tree with an effective amount of 3-(difluoromethyl)-1-methyl-N-[(3R)-1,1,3-trimethyl-2,3-dihydroinden-4-yl]pyrazole-4-carboxamide and a surfactant.

20 Claims, No Drawings

METHODS FOR APPLE SCAB CONTROL

FIELD OF THE INVENTION

The present invention generally relates to methods for controlling apple scab caused by *Venturia inaequalis* comprising spraying the bark of an apple tree with an effective amount of 3-(difluoromethyl)-1-methyl-N-[(3R)-1,1,3-trimethyl-2,3-dihydroinden-4-yl]pyrazole-4-carboxamide.

BACKGROUND OF THE INVENTION

Apple scab, caused by the fungus *Venturia inaequalis*, is a major problem for growers of apple trees. Apple scab causes dark lesions on the leaves, bark, buds and fruit of the trees. The disease causes significant crop yield losses each year because the infected fruit is not marketable. The disease also causes damage to ornamental apple trees.

There are generally two phases to apple scab infection. When the temperatures begin to warm up, *Venturia inaequalis* spores are blown onto the bark and leaves of the apple trees. Later in the season, secondary infections begin as the fungi release more spores which infect new fruit and additional leaves.

Currently, it is very difficult to control apple scab for several reasons. First, *Venturia inaequalis* has developed resistance to some fungicides, such as benzimidazole and strobilurin/quinone fungicides. Secondly, some effective fungicides, such as benzimidazole fungicides, are being banned in some areas because they are harmful to the environment or humans.

Yet another issue is that often the currently available treatments have to be re-applied repeatedly to be effective and in order to treat secondary infections. Some apple orchards are treated with fungicides for apple scab up to 12 times in a growing season. The extra applications add to the expense of disease control because more of the product must be purchased, and significant time and labor resources are used during the subsequent applications. Further, each new application increases the risk of exposure of the product to non-target trees.

Another problem is that some treatments require that the leaves and fruit be treated. For example, some contact fungicides, such as Captan (N-trichtoromethylthiocyclohexene-1,2-dicarboximide, available from Southern Agricultural Insecticides, Inc.), are effective against apple scab. However, Captan has no systemic control activity so it must be applied directly and repeatedly to the infected areas. A lot of product must be used and the techniques are often dangerous and/or wasteful. For example, if a tree's leaves are infected, comprehensive treatment requires application of the product to the leaf surface. Given the size of trees, it is difficult to apply the product to the leaves. One application method requires the user to tediously spray the leaves with a low pressure sprayer in close proximity to each leaf. For a home owner or backyard gardener, this method may require the user to use a ladder or other tool to elevate himself to the leaves. The user must be careful not to damage the tree by climbing or other similar means of accessing the leaves. Alternatively, a high pressure sprayer could be used. For this application method, the user could be on the ground, however, this method results in drift of the product to the surrounding area. The drift can require that people, animals, and non-target tree species be removed from the area of treatment or otherwise protected from the product by sufficient physical barriers. These additional measures required for safe and effective foliar spray applications are costly and inconvenient.

In the past, bark spray applications have been used with limited success. The treatments resulted in ineffective or unpredictable disease control in trees because the fungicides were not able to penetrate the tree bark and/or the tree could not transfer them to the areas in need of treatment.

Other means of treating trees are available but have proven to be ineffective or impractical to implement. Some methods require professionals who are trained in specialized equipment to apply the product. Other expensive methods include invasive drilling, bark injections, or high-pressure root flare injections. For example, there has been a fungicide that provided some systemic fungal protection, however, it was effective only when injected directly into the tree.

3-(Difluoromethyl)-1-methyl-N-[(3R)-1,1,3-trimethyl-2,3-dihydroinden-4-yl]pyrazole-4-carboxamide has the following structure:

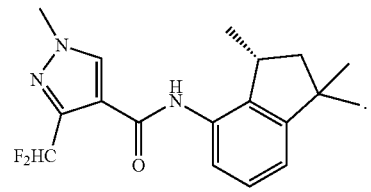 [SMILES: C[C@@H]1CC(C)(C)c2cccc(NC(=O)c3cn(C)nc3C(F)F)c21]

U.S. Pat. No. 8,580,836 discloses that carboxamide compounds can be sprayed to the bark of trees to control diseases. This patent, however, fails to disclose or suggest the use of 3-(difluoromethyl)-1-methyl-N-[(3R)-1,1,3-trimethyl-2,3-dihydroinden-4-yl]pyrazole-4-carboxamide to treat apple scab by bark spray treatment.

Therefore, there is a need in the art for safe and effective methods for providing long-term and systemic protection to apple trees from apple scab infection.

SUMMARY OF THE INVENTION

In one aspect, the present invention is directed to methods for controlling apple scab caused by *Venturia inaequalis* comprising spraying the bark of an apple tree with an effective amount of 3-(difluoromethyl)-1-methyl-N-[(3R)-1,1,3-trimethyl-2,3-dihydroinden-4-yl]pyrazole-4-carboxamide and a surfactant.

In another aspect, the present invention is directed to methods for controlling apple scab caused by *Venturia inaequalis* comprising spraying the bark of a dormant apple tree with from about 0.0001 to about 1 gram of 3-(difluoromethyl)-1-methyl-N-[(3R)-1,1,3-trimethyl-2,3-dihydroinden-4-yl]pyrazole-4-carboxamide per centimeter of tree trunk diameter at breast height and from about 0.25 to about 10% volume per volume of a surfactant.

DETAILED DESCRIPTION OF THE INVENTION

Applicants unexpectedly found that 3-(difluoromethyl)-1-methyl-N-[(3R)-1,1,3-trimethyl-2,3-dihydroinden-4-yl] pyrazole-4-carboxamide when combined with a surfactant and applied as a bark spray, exhibited excellent activity against apple scab caused by *Venturia inaequalis* as compared to metconazole and propiconazole. 3-(Difluoromethyl)-1-methyl-N-[(3R)-1,1,3-trimethyl-2,3-dihydroinden- 4-yl]pyrazole-4-carboxamide provides desirable broad spectrum apple scab control when applied according to the present invention. This finding was unexpected because of the low water solubility of 3-(difluoromethyl)-1-methyl-N-[(3R)-1,1,3-trimethyl-2,3-dihydroinden-4-yl]pyrazole-4-carboxamide, very low application rate, and high level of control obtained. Further, it was very unexpected that the apple trees would be able to transport 3-(difluoromethyl)-1-methyl-N-[(3R)-1,1,3-trimethyl-2,3-dihydroinden-4-yl]pyrazole-4-carboxamide to the leaves and fruit in the canopy at levels to provide disease control.

Another advantage of the present invention is that the trees can be sprayed when they are dormant. Frequently, apple tree growers have more time and resources when the trees are dormant so the methods of the present invention are especially convenient for tree growers.

A further advantage of the present invention is that because the trees translocate and do not immediately break down 3-(difluoromethyl)-1-methyl-N-[(3R)-1,1,3-trimethyl-2,3-dihydroinden-4-yl]pyrazole-4-carboxamide, the trees may need fewer sequential foliar fungicide applications or only need one or two treatments per this present invention for systemic, all-season control.

Yet another advantage of the present invention is that the trees can be treated by spraying only the base of their trunks. This method reduces waste and contact of the 3-(difluoromethyl)-1-methyl-N-[(3R)-1,1,3-trimethyl-2,3-dihydroinden-4-yl]pyrazole-4-carboxamide to non-target species in proximity to the trees.

In an embodiment, the present invention is directed to methods for controlling apple scab caused by *Venturia inaequalis* comprising spraying the bark of an apple tree with an effective amount of 3-(difluoromethyl)-1-methyl-N-[(3R)-1,1,3-trimethyl-2,3-dihydroinden-4-yl]pyrazole-4-carboxamide and a surfactant.

In another preferred embodiment, the effective amount of 3-(difluoromethyl)-1-methyl-N-[(3R)-1,1,3-trimethyl-2,3-dihydroinden-4-yl]pyrazole-4-carboxamide is from about 0.0001 to about 1 grams per centimeter of tree trunk diameter at breast height. In a more preferred embodiment, the effective amount of 3-(difluoromethyl)-1-methyl-N-[(3R)-1,1,3-trimethyl-2,3-dihydroinden-4-yl]pyrazole-4-carboxamide is from about 0.001 to about 0.01 grams per centimeter of trunk diameter at breast height. In a most preferred embodiment, the effective amount of 3-(difluoromethyl)-1-methyl-N-[(3R)-1,1,3-trimethyl-2,3-dihydroinden-4-yl]pyrazole-4-carboxamide is from about 0.003 to about 0.03 grams per centimeter of trunk diameter at breast height.

Suitable apple tree varieties include, but are not limited to, braeburn, cameo, cortland, crabapple, empire, Fuji, gala, ginger gold, golden delicious, granny smith, honeycrisp, idared, jonagold, jonathan, McIntosh, mutsu, nittany, pink lady, rome, red delicious, stayman, winesap, and york.

In yet another embodiment, the apple tree is sprayed with an effective amount of 3-(difluoromethyl)-1-methyl-N-[(3R)-1,1,3-trimethyl-2,3-dihydroinden-4-yl]pyrazole-4-carboxamide and surfactant when the tree is dormant. As used herein, "dormant" refers to a period in the tree's life cycle when the tree has a significantly slowed metabolism. Leaves may or may not be present on the tree at the time of application.

In an alternative embodiment, the apple tree is sprayed with an effective amount of 3-(difluoromethyl)-1-methyl-N-[(3R)-1,1,3-trimethyl-2,3-dihydroinden-4-yl]pyrazole-4-carboxamide and surfactant during the time between when the tree is dormant after leaf drop in the fall until the time when it produces leaf buds which typically occurs in the spring season of the year.

In yet another embodiment, the apple tree is sprayed with an effective amount of 3-(difluoromethyl)-1-methyl-N-[(3R)-1,1,3-trimethyl-2,3-dihydroinden-4-yl]pyrazole-4-carboxamide and surfactant during the time between when the tree is dormant up until the time when bud swell begins in the spring of the year.

In embodiments of the present invention, the dormant apple trees may be sprayed with high or low pressure (meaning lower than 40 psi) spraying mechanisms. A backpack sprayer or similar sprayer can be used for ease of the person delivering the spray to the tree bark.

In a further embodiment, the apple tree is sprayed on the lower 150 centimeters of the trunk. In a more preferred embodiment, the apple tree is sprayed on the lower 100 centimeters of the trunk.

In yet another embodiment, the 3-(difluoromethyl)-1-methyl-N-[(3R)-1,1,3-trimethyl-2,3-dihydroinden-4-yl]pyrazole-4-carboxamide may be mixed with a solvent prior to application. One presently preferred solvent is water.

In a preferred embodiment, the effective amount of 3-(difluoromethyl)-1-methyl-N-[(3R)-1,1,3-trimethyl-2,3-dihydroinden-4-yl]pyrazole-4-carboxamide is from about 10 to about 1,000 parts per million active ingredient solution concentration. In a more preferred embodiment, the effective amount of 3-(difluoromethyl)-1-methyl-N-[(3R)-1,1,3-trimethyl-2,3-dihydroinden-4-yl]pyrazole-4-carboxamide is from about 25 to about 500 parts per million active ingredient solution concentration. In a most preferred embodiment, the effective amount of 3-(difluoromethyl)-1-methyl-N-[(3R)-1,1,3-trimethyl-2,3-dihydroinden-4-yl]pyrazole-4-carboxamide is from about 50 to about 200 parts per million active ingredient solution concentration.

In an embodiment, from about 0.25 to about 10% volume per volume concentration surfactant in the spray solution is applied to the tree. In a preferred embodiment, from about 0.1 to about 5% volume per volume concentration surfactant in the spray solution is applied to the tree. In a more preferred embodiment, from about 1 to about 2.5% volume per volume concentration surfactant in the spray solution is applied to the tree.

Suitable surfactants include, but are not limited to, mixtures of alkylphenol ethoxylate, polysiloxane polyether copolymers, and propylene glycol; polyether modified polysiloxanes; hexylene glycols; dipropylene glycols; ethoxylated alcohols; and combinations thereof. One presently preferred surfactant is a mixture of alkylphenol ethoxylate, polysiloxane polyether copolymers, and propylene glycol.

In an embodiment, 3-(difluoromethyl)-1-methyl-N-[(3R)-1,1,3-trimethyl-2,3-dihydroinden-4-yl]pyrazole-4-carboxamide and the surfactant may be mixed with a another fungicide. In a preferred embodiment, the fungicide is a triazole fungicide. Two presently preferred triazole fungicides are metconazole and propiconazole.

In another preferred embodiment, 3-(difluoromethyl)-1-methyl-N-[(3R)-1,1,3-trimethyl-2,3-dihydroinden-4-yl]pyrazole-4-carboxamide and the surfactant may be mixed with a phosphonate fungicide. In a preferred embodiment, the phosphonate fungicide comprises mono and dipotassium salts of phosphorous acid (for example, Agri-Fos®, AgriFos is available from and a registered trademark of AgBio).

In a further embodiment, 3-(difluoromethyl)-1-methyl-N-[(3R)-1,1,3-trimethyl-2,3-dihydroinden-4-yl]pyrazole-4-carboxamide and the surfactant may be mixed with an inhibitor of succinate-dehydrogenase. Preferably, the inhibitor of succinate-dehydrogenase is selected from the group consisting of penflufen, isopyrazam, benzovindiflupyr, bixafen, sedaxane, fluxapyroxad, fluopyram, penthiopyrad, boscalid, N-[1-(2,4-dichlophenyl)-1-methoxypropan-2-yl]-3-(difluoromethyl)-1-methyl-1H-pyrazole-4-carboxamide, N-[9-(dichloromethylene)-1,2,3,4-tetrahydro-1,4-methanonaphthalen-5-yl]-3-(difluoromethyl)-1-methyl-1H-pyrazole-4-carboxamide, N-[(1S,4R)-9-(dichlormethylen)-1,2,3,4-tetrahydro-1,4-methanonaphthalen-5-yl]-3-(difluoromethyl)-1-methyl-1H-pyrazol-4-carboxamide, and N-[(1R,4S)-9-(dichlormethylen)-1,2,3,4-tetrahydro-1,4-methanonaphthalen-5-yl]-3-(difluoromethyl)-1-methyl-1H-pyrazol-4-carboxamide.

In an embodiment, 3-(difluoromethyl)-1-methyl-N-[(3R)-1,1,3-trimethyl-2,3-dihydroinden-4-yl]pyrazole-4-carboxamide and the surfactant may be mixed with an insecticide. One preferred class of insecticides is neonicotinoids. More preferably, the neonicotinoid is selected from the group consisting of clothianidin, imidacloprid, thiacloprid, dinotefuran, acetamiprid, nitenpyram and thiamethoxam.

In a further embodiment, 3-(difluoromethyl)-1-methyl-N-[(3R)-1,1,3-trimethyl-2,3-dihydroinden-4-yl]pyrazole-4-carboxamide is mixed with a strobilurin. Preferably, the strobilurin is selected from the group consisting of azoxystrobin, trifloxystrobin, fluoxastrobin, mandestrobin, picoxystrobin, pyraclostrobin, dimoxystrobin, metominostrobin and orysastrobin.

In a further embodiment, the present invention is directed to methods for controlling apple scab caused by *Venturia inaequalis* comprising spraying the bark of a dormant apple tree with from about 0.0001 to about 1 grams of 3-(difluoromethyl)-1-methyl-N-[(3R)-1,1,3-trimethyl-2,3-dihydroinden-4-yl]pyrazole-4-carboxamide per centimeter of tree trunk diameter at breast height and from about 0.25 to about 10% volume per volume surfactant, wherein the surfactant is a mixture of alkylphenol ethoxylate, polysiloxane polyether copolymers, and propylene glycol.

In yet another embodiment, the present invention is directed to methods for controlling apple scab caused by *Venturia inaequalis* comprising spraying the bark of a dormant apple tree with from about 10 to about 1,000 parts per million active ingredient solution concentration of 3-(difluoromethyl)-1-methyl-N-[(3R)-1,1,3-trimethyl-2,3-dihydroinden-4-yl]pyrazole-4-carboxamide and from about 0.25 to about 10% volume per volume concentration in the spray solution of a surfactant, wherein the surfactant is a mixture of alkylphenol ethoxylate, polysiloxane polyether copolymers, and propylene glycol.

As used herein, "yield" refers to an increase in the amount or number of apples that are marketable.

As used herein, "controlling apple scab" refers to reducing the amount of damage caused by apple scab to a level that is acceptable to the grower. For example, "controlling apple scab" can mean the prevention of the fungal infection, the treatment of an existing infection, limiting the spread of the infection, or the use of the methods as a prophylactic.

Throughout the application, the singular forms "a," "an," and "the" include plural reference unless the context clearly dictates otherwise.

As used herein, all numerical values relating to amounts, weight percentages and the like, are defined as "about" or "approximately" each particular value, plus or minus 10%. For example, the phrase "at least 5.0% by weight" is to be understood as "at least 4.5% to 5.5% by weight." Therefore, amounts within 10% of the claimed values are encompassed by the scope of the claims.

The invention will be understood more clearly from the following non-limiting representative examples. Of course, the present invention is not limited to the particular embodiments and modes of operation described herein and it is possible to imagine a number of variations in the details without departing from the scope of this invention.

The examples below are presented to describe preferred embodiments and utilities of the invention and are not meant to limit the invention unless otherwise stated in the claims appended hereto.

EXAMPLES

A 40% suspension concentrate formulation was used as the source of 3-(difluoromethyl)-1-methyl-N-[(3R)-1,1,3-trimethyl-2,3-dihydroinden-4-yl]pyrazole-4-carboxamide (available from Sumitomo Chemical Company, Tokyo, Japan).

Tourney® fungicide (Tourney® is available from Valent U.S.A. Corporation, Tourney is a registered trademark of Valent U.S.A. Corporation) was used as the source of metconazole.

Tilt® fungicide (Tilt® is available from Syngenta Corporation, Tilt is a registered trademark of Syngenta Corporation) was used as the source of propiconazole.

Pentra-Bark® surfactant (Pentra-Bark® surfactant is available from AgBio, Inc., Pentra-Bark is a registered trademark of Quest Products Corporation) was used as the source of surfactant in the following examples. PentraBark® surfactant is a mixture of alkylphenol ethoxylate, polysiloxane polyether copolymers, and propylene glycol.

Example 1

Applicant conducted the following study to determine the effect of a 3-(difluoromethyl)-1-methyl-N-[(3R)-1,1,3-trimethyl-2,3-dihydroinden-4-yl]pyrazole-4-carboxamide bark spray application on common fungal infections in apple and pear trees. Applications were made in late February with a $CO_2$ charged, single-tip hand sprayer. Treatments were applied as a spray to the lower 3 to 4 feet of the tree trunks all the way around the tree. The tree trunks were sprayed until they were wet. If the treatments included a surfactant (see tables), then the treatments included a surfactant at a rate of 3 fl oz/gallon of the spray mix. The apple trees were at bed swell stage. The apple tree trunks were about 5 to 8 inches in diameter. The pear trees were at mid-petal fall with some green leaves emerging. The pear tree trunks were about 10 to 12 inches in diameter. The following rates in grams per active/cm diameter tree trunk are based on an average trunk diameter. A large amount of apple scab naturally developed during this growing season in this location. The effects of the treatments on apple leaf phytotoxicity, apple leaf apple scab incidence, apple leaf scab severity, and apple leaf percent control were observed 113 and 169 days after treatment ("DAT"). The results of this study are below in Tables 1 and 2.

TABLE 1

| Treatment | Rate (grams active/cm trunk diameter) | 113 DAT | | | |
| --- | --- | --- | --- | --- | --- |
| | | Apple Leaf Phyto-toxicity | Apple Leaf scab incidence | Apple leaf scab severity | Apple leaf % control |
| Control Surfactant | 2.3% V/V | 0 | 33.33 | 33.33 | 0 |

TABLE 1-continued

| Treatment | Rate (grams active/cm trunk diameter) | 113 DAT Apple Leaf Phyto-toxicity | Apple Leaf scab incidence | Apple leaf scab severity | Apple leaf % control |
|---|---|---|---|---|---|
| Metconazole + Surfactant | 0.86 + 2.3% V/V | 0 | 12.5 | 10 | 80 |
| Metconazole + Surfactant | 1.72 + 2.3% V/V | 0 | 18 | 18.3 | 68.8 |
| Metconazole + Surfactant | 3.44 + 2.3% V/V | 0 | 11.25 | 13.3 | 80 |
| 3-(difluoromethyl)-1-methyl-N-[(3R)-1,1,3-trimethyl-2,3-dihydroinden-4-yl]pyrazole-4-carboxamide + Surfactant | 0.003 + 2.3% V/V | 0 | 20 | 13.8 | 88.3 |
| 3-(difluoromethyl)-1-methyl-N-[(3R)-1,1,3-trimethyl-2,3-dihydroinden-4-yl]pyrazole-4-carboxamide + Surfactant | 0.03 + 2.3% V/V | 0 | 23 | 16.3 | 80 |
| Propiconazole + Surfactant | 1.16 + 2.3% V/V | 0 | 18.78 | 8.3 | 68.3 |

TABLE 2

| Treatment | Rate (grams active/cm trunk diameter) | 169 DAT Apple Leaf Phyto-toxicity | Apple Leaf scab incidence | Apple leaf scab severity | Apple leaf % control |
|---|---|---|---|---|---|
| Control Surfactant | 2.3% V/V | 0 | 25.75 | 9.25 | 0 |
| Metconazole + Surfactant | 0.86 + 2.3% V/V | 0 | 18.88 | 4.25 | 31.3 |
| Metconazole + Surfactant | 1.7 + 2.3% V/V | 0 | 15.5 | 4.75 | 27.5 |
| Metconazole + Surfactant | 3.4 + 2.3% V/V | 0 | 7.25 | 2.75 | 62.5 |
| 3-(difluoromethyl)-1-methyl-N-[(3R)-1,1,3-trimethyl-2,3-dihydroinden-4-yl]pyrazole-4-carboxamide + Surfactant | 0.003 + 2.3% V/V | 0 | 13.75 | 7 | 43.8 |
| 3-(difluoromethyl)-1-methyl-N-[(3R)-1,1,3-trimethyl-2,3-dihydroinden-4-yl]pyrazole-4-carboxamide + Surfactant | 0.03 + 2.3% V/V | 0 | 13.75 | 4.5 | 46.3 |
| Propiconazole + Surfactant | 1.16 + 2.3% V/V | 0 | 13.38 | 4.63 | 36.3 |

On apple trees, Applicant found that 3-(difluoromethyl)-1-methyl-N-[(3R)-1,1,3-trimethyl-2,3-dihydroinden-4-yl]pyrazole-4-carboxamide provided considerable (80 to 88%) control of apple scab. On pear trees, Applicant found that when 3-(difluoromethyl)-1-methyl-N-[(3R)-1,1,3-trimethyl-2,3-dihydroinden-4-yl]pyrazole-4-carboxamide was applied at this rate and at this time of development, the treatment failed to provide adequate control of Fabraea leaf spot or *Alternaria* leaf spot.

Example 2

In this study, the 3-(difluoromethyl)-1-methyl-N-[(3R)-1,1,3-trimethyl-2,3-dihydroinden-4-yl]pyrazole-4-carboxamide treatment was applied at the time of bud swell in mid March on apple tree trunks (treatment 5). The result of this treatment was compared to metconazole treatments applied when the apple trees were dormant (treatments 2 and 3), at the time of bud swell (treatment 4), and a foliar spray applied after petal fall (treatment 6). The control treatment (treatment 1) was applied during bud swell, as well. Four trees were subjected to each treatment.

TABLE 3

| | Treatment | Rate (grams active/cm trunk diameter) | Phytotoxicity | Leaf pest incidence | Leaf pest severity | Fruit pest incidence | Fruit pest severity | Fruit pest incidence | Fruit pest severity |
|---|---|---|---|---|---|---|---|---|---|
| 1 | Control Surfactant | 2.3% V/V | 0 | 4.750 | 10.8 | 37.50 | 2.5 | 46.67 | 3.0 |
| 2 | Metconazole + Surfactant | 1.72 + 2.3% V/V | 0 | 1.875 | 5.0 | 33.75 | 2.25 | 45.0 | 3.0 |
| 3 | Metconazole + Surfactant | 1.72 + 2.3% V/V | 0 | 1.000 | 1.7 | 6.67 | 0.333 | 10.0 | 0.5 |
| 4 | Metconazole + Surfactant | 1.72 + 2.3% V/V | 0 | 0.140 | 2.0 | 14.00 | 1.125 | 18.67 | 1.5 |
| 5 | 3-(difluoromethyl)-1-methyl-N-[(3R)-1,1,3-trimethyl-2,3-dihydroinden- | 0.003 + 2.3% V/V | 0 | 0.25 | 0.3 | 10.25 | 0.638 | 0.33 | 0.183 |

TABLE 3-continued

| | Treatment | Rate (grams active/cm trunk diameter) | Phytotoxicity | Leaf pest incidence | Leaf pest severity | Fruit pest incidence | Fruit pest severity | Fruit pest incidence | Fruit pest severity |
|---|---|---|---|---|---|---|---|---|---|
| | 4-yl]pyrazole-4-carboxamide + Surfactant | | | | | | | | |
| 6 | Metconazole | 4 oz pr/A | 0 | 0.125 | 0.8 | 2.75 | 0.263 | 3.67 | 0.350 |

This study showed a large reduction in leaf pest incidence, leaf pest severity, fruit pest severity, fruit pest incidence, and fruit pest severity.

The invention claimed is:

1. A method of controlling apple scab caused by *Venturia inaequalis* comprising spraying the bark of an apple tree with an effective amount of 3-(difluoromethyl)-1-methyl-N-[(3R)-1,1,3-trimethyl-2,3-dihydroinden-4-yl]pyrazole-4-carboxamide and a surfactant.

2. The method of claim 1 wherein the effective amount of 3-(difluoromethyl)-1-methyl-N-[(3R)-1,1,3-trimethyl-2,3-dihydroinden-4-yl]pyrazole-4-carboxamide is from about 0.0001 to about 1 gram of 3-(difluoromethyl)-1-methyl-N-[(3R)-1,1,3-trimethyl-2,3-dihydroinden-4-yl]pyrazole-4-carboxamide per centimeter of the trunk diameter at breast height.

3. The method of claim 2 wherein the effective amount of 3-(difluoromethyl)-1-methyl-N-[(3R)-1,1,3-trimethyl-2,3-dihydroinden-4-yl]pyrazole-4-carboxamide is from about 0.001 to about 0.01 grams of 3-(difluoromethyl)-1-methyl-N-[(3R)-1,1,3-trimethyl-2,3-dihydroinden-4-yl]pyrazole-4-carboxamide per centimeter of the trunk diameter at breast height.

4. The method of claim 1 wherein the apple tree is selected from the group consisting of braeburn, cameo, cortland, crabapple, empire, Fuji, gala, ginger gold, golden delicious, granny smith, honeycrisp, idared, jonagold, jonathan, McIntosh, mutsu, nittany, pink lady, rome, red delicious, stayman, winesap, and york.

5. The method of claim 1 wherein the tree is sprayed when the tree is dormant.

6. The method of claim 1 wherein the tree is sprayed on the lower 150 centimeters of the trunk.

7. The method of claim 1 wherein the 3-(difluoromethyl)-1-methyl-N-[(3R)-1,1,3-trimethyl-2,3-dihydroinden-4-yl]pyrazole-4-carboxamide is mixed with a solvent prior to application.

8. The method of claim 7 wherein the solvent is water.

9. The method of claim 7 wherein the concentration of 3-(difluoromethyl)-1-methyl-N-[(3R)-1,1,3-trimethyl-2,3-dihydroinden-4-yl]pyrazole-4-carboxamide is from about 10 to about 1,000 parts per million active ingredient.

10. The method of claim 1 wherein the surfactant is a mixture of alkylphenol ethoxylate, polysiloxane polyether copolymers, and propylene glycol.

11. The method of claim 1 wherein the 3-(difluoromethyl)-1-methyl-N-[(3R)-1,1,3-trimethyl-2,3-dihydroinden-4-yl]pyrazole-4-carboxamide is mixed with a triazole fungicide.

12. The method of claim 11 wherein the triazole fungicide is metconazole.

13. The method of claim 1 wherein the 3-(difluoromethyl)-1-methyl-N-[(3R)-1,1,3-trimethyl-2,3-dihydroinden-4-yl]pyrazole-4-carboxamide is mixed with an inhibitor of succinate-dehydrogenase.

14. The method of claim 13 wherein the inhibitor of succinate-dehydrogenase is selected from the group consisting of penflufen, isopyrazam, bixafen, sedaxane, fluxapyroxad, fluopyram, penthiopyrad, boscalid, N-[1-(2,4-dichlohenyl)-1-methoxypropan-2-yl]-3-(difluoromethyl)-1-methyl-1H-pyrazole-4-carb oxamide, N-[9-(dichloromethylene)-1,2,3,4-tetrahydro-1,4-methanonaphthalen-5-yl]-3-(difluoromethyl)-1-methyl-1H-pyrazole-4-carboxamide, N-[(1S,4R)-9-(dichlormethylen)-1,2,3,4-tetrahydro-1,4-methanonaphthalen-5-yl]-3-(difluormethyl)-1-methyl-1H-pyrazol-4-carboxamid, and N-[(1R,4S)-9-(dichlormethylen)-1,2,3,4-tetrahydro-1,4-methanonaphthalen-5-yl]-3-(difluormethyl)-1-methyl-1H-pyrazol-4-carboxamid.

15. The method of claim 1 wherein the 3-(difluoromethyl)-1-methyl-N-[(3R)-1,1,3-trimethyl-2,3-dihydroinden-4-yl]pyrazole-4-carboxamide is mixed with an insecticide.

16. The method of claim 15 wherein the insecticide is a neonicotinoid.

17. The method of claim 16 wherein the neonicotinoid is selected from the group consisting of clothianidin, imidacloprid, thiacloprid, dinotefuran, acetamiprid, nitenpyram and thiamethoxam.

18. The method of claim 1 wherein the 3-(difluoromethyl)-1-methyl-N-[(3R)-1,1,3-trimethyl-2,3-dihydroinden-4-yl]pyrazole-4-carboxamide is mixed with a strobilurin.

19. The method of claim 18 wherein the strobilurin is selected from the group consisting of azoxystrobin, trifloxystrobin, fluoxastrobin, mandestrobin, picoxystrobin, pyraclostrobin, dimoxystrobin, metominostrobin and orysastrobin.

20. A method of controlling apple scab caused by *Venturia inaequalis* comprising spraying the bark of a dormant apple tree with from about 0.0001 to about 1 grams of 3-(difluoromethyl)-1-methyl-N-[(3R)-1,1,3-trimethyl-2,3-dihydroinden-4-yl]pyrazole-4-carboxamide per cm diameter of tree trunk diameter and from about 0.25 to about 10 percent volume per volume of a surfactant, wherein the surfactant is a mixture of alkylphenol ethoxylate, polysiloxane polyether copolymers, and propylene glycol.

* * * * *